United States Patent [19]

Davis et al.

[11] Patent Number: 5,083,470
[45] Date of Patent: Jan. 28, 1992

[54] CAPACITIVE LIQUID LEVEL SENSOR

[75] Inventors: James E. Davis, Wilmington; Stephen J. Simko, Bear, both of Del.

[73] Assignee: E. I. Du Pont de Nemours and Company, Wilmington, Del.

[21] Appl. No.: 590,439

[22] Filed: Sep. 28, 1990

Related U.S. Application Data

[63] Continuation of Ser. No. 466,936, Jan. 18, 1990, abandoned.

[51] Int. Cl.⁵ .............................................. B01L 3/02
[52] U.S. Cl. .............................................. 73/864.24
[58] Field of Search .......... 73/863.01, 864.23–864.25, 73/304 C, 290 R; 361/284; 422/63, 67, 100; 324/672, 674, 679, 681, 683

[56] References Cited

U.S. PATENT DOCUMENTS

| | | |
|---|---|---|
| 3,391,547 | 7/1968 | Kingston . |
| 3,635,094 | 1/1972 | Oberli ............................... 73/863.01 |
| 3,939,360 | 2/1976 | Jackson ............................... 361/278 |
| 4,099,167 | 7/1978 | Pomerantz et al. ............... 73/304 C |
| 4,325,909 | 4/1982 | Coulter et al. .................... 73/864.24 |
| 4,326,851 | 4/1982 | Bello et al. .......................... 422/64 |
| 4,635,478 | 1/1987 | Hope ................................. 73/292 |
| 4,736,638 | 4/1988 | Okawa et al. .................... 73/864.24 |
| 4,818,492 | 4/1989 | Shimizu ............................. 422/100 |
| 4,829,837 | 5/1989 | Telfer ................................ 73/304 C |
| 4,873,875 | 10/1989 | Cork ................................ 73/864.23 |
| 4,912,976 | 4/1990 | Labriola, II ...................... 324/675 |

FOREIGN PATENT DOCUMENTS

| | | | |
|---|---|---|---|
| 00039184 | 4/1978 | Japan ............................... 73/863.01 |
| 0039185 | 4/1978 | Japan ............................... 73/863.01 |
| 0108754 | 6/1985 | Japan ............................... 73/863.01 |
| 2066961 | 7/1981 | United Kingdom .............. 73/304 C |

Primary Examiner—Robert Raevis

[57] ABSTRACT

A capacitance liquid level sensor uses an inductance to isolate the probe of the sensor from the plastic tubing coupled to the probe thus reducing false signals generated by movement of the tubing.

2 Claims, 2 Drawing Sheets

CAPACITIVE LIQUID LEVEL SENSOR

CROSS-REFERENCE TO RELATED APPLICATIONS

This application is a continuation of application Ser. No. 466,936, filed Jan. 18, 1990, now abandoned.

BACKGROUND OF THE INVENTION

This invention relates to capacitive liquid level sensors. Such liquid level sensors find use in many instruments wherein a robotic probe is used to withdraw liquid from a container holding a sample to be analyzed or a reagent.

In such robotic systems, it is desirable to have knowledge of the level of the liquid in the container such that the probe used to withdraw the liquid can be controlled to minimize contact with the contents of the container. In this manner cross contamination between samples and reagents is reduced and the job of washing the probe tip is made easy. In such robotic systems the probe is introduced into the liquid container and preferably maintained just below the surface of the liquid.

To accomplish this objective, various level sensors have been developed. Among those are the so-called capacitive level sensors. These are based on the fact that any conductor exhibits a finite electrical capacitance. When the probe actually touches a liquid, the higher dielectric constant and greater surface area of the liquid results in an increased probe capacitance. These capacitance changes can be rather small so that sensitive detection devices are required.

Devices known in the prior art that are suitable for detecting small changes in capacitance include bridges, RC or LC oscillators and frequency meter counters (including heterodyning), phase locked loops, zero crossing periodometers, amplitude changes to an RC or LC filter, and phase shift changes through an RC or LC circuit.

Among the prior art capacitive liquid level sensors is Kingston U.S. Pat. No. 3,391,547 which discloses a capacitive liquid level probe for a liquid tank. He utilizes a capacitor probe, disposed in the liquid, as one leg of a bridge circuit. An unbalance in the circuit, as a result of change in capacitance of the probe, is detected by a phase sensitive detector which is referenced by a fixed frequency excitation oscillator through a variable phase shifter. The variable phase shifter allows for offset adjustment.

In similar manner, Oberli U.S. Pat. No. 3,635,094 discloses a capacitive level sense means for an automatic transfer pipette. The sample probe is utilized as the first element and a metal stand around the sample vessel is the second element which forms a capacitor in one leg of a bridge circuit. The remaining legs of the bridge consist of a variable capacitor leg and two resistor legs. The variable capacitor leg may be adjusted such that its capacitance matches that of the probe contacting the liquid. The bridge circuit is excited by a fixed frequency oscillator and a differential amplifier is utilized to determine when the bridge is balanced indicating that the probe has contacted the liquid.

Bello et al. U.S. Pat. No. 4,326,851 discloses a level sense apparatus and method for use in an automatic clinical analyzer in which a variable capacitor is formed by a grounded probe and a metal plate, which is connected to the detection circuit, disposed below the sample vessel. A fixed frequency excitation signal is utilized and the capacitance change of the metal probe resulting from the probe contacting the liquid is detected as a voltage change in the detection circuit. This arrangement presents a problem in that spills on the electrode or supply tray can change the circuits operation and the circuit requires the use of shielding pads.

Another U.S. patent, Okawa et al. U.S. Pat. No. 4,736,638 discloses a liquid level sense apparatus for use in an automatic clinical analyzer. A metal plate disposed under the sample vessel and connected to a fixed frequency oscillator emits low frequency electromagnetic radiation up through the sample. The dispense probe serves as an antenna and is connected to a detection circuit, having appropriate bandpass filtering, which detects a voltage amplitude change when the probe contacts the liquid sample. This circuit has many of the disadvantages of Bello. In addition, the use of low frequency limits the time response of the circuit.

Finally, Shimizu U.S. Pat. No. 4,818,492 discloses a capacitive liquid level sensor for an automatic clinical analyzer. He utilizes a resistor bridge with a fixed frequency oscillator exciting one diagonal of the bridge and the probe serving as a capacitor across the other diagonal. Phase shift across the capacitor (probe), as a result of change in capacitance of the probe, is detected by a phase detector which is referenced by the fixed frequency excitation oscillator through a variable phase shifter. The variable phase shifter allows for offset adjustment. The output of the phase detector is filtered and compared against a reference value to provide a signal indicating the presence of liquid at the probe.

The problem with many of these prior sensors is that they have to be run at relatively high frequencies in order to have the sensitivity required to detect liquid levels. This causes them to be sensitive to changes in capacitance of the flexible plastic tubing that couples the sucking probe to the suction pump. Hence the simple motion of the tubing as the probe is raised and lowered causes false levels to be indicated. This limits the sensitivity of the probe.

SUMMARY OF THE INVENTION

Many of these false level sensing problems associated with the prior art capacitive liquid level sensors are reduced by the subject invention which isolates the probe from the connecting tubing by the use of an element exhibiting inductive reactance.

According to this invention, a capacitive liquid level sensor for a liquid pipetting system comprises: a pipette probe for withdrawing liquid from a sample, means coupled to the pipette probe for applying suction, an oscillator coupled to the probe for applying a high frequency signal to the probe, the amplitude and/or phase of the oscillator being affected by the capacitance of the probe, comparator means for generating a level sensor signal according to the amplitude or phase of the oscillator for signaling the probe's reaching the liquid level of the sample, and means exhibiting an inductive reactance positioned on the probe adjacent to the suction means, thereby to isolate the probe from the withdrawing means.

In a preferred embodiment of the invention, the suction means is plastic tubing and the reactance means is a ferrite toroid positioned about the metallic probe. Alternatively, the plastic tubing itself may be coiled to form the inductor. To improve the inductance, the coiled tube may be disposed in a "pot core" ferrite. Also, a piece of metal tubing may be connected in series with the plastic tubing and grounded. These features have the advantage when a toroid is used of reducing the portion of the probe that carries RF voltage so that RF radiation is reduced. Also, since the probe does not have to be insulated from its mount, a more robust mounting can be used.

DESCRIPTION OF THE DRAWINGS

A more complete understanding of the invention and its advantages may be understood in connection with the accompanying drawings in which:

FIG. 3 is a pictorial diagram of an alternative embodiment to FIG. 1.

DESCRIPTION OF THE PREFERRED EMBODIMENT

Figure 1:
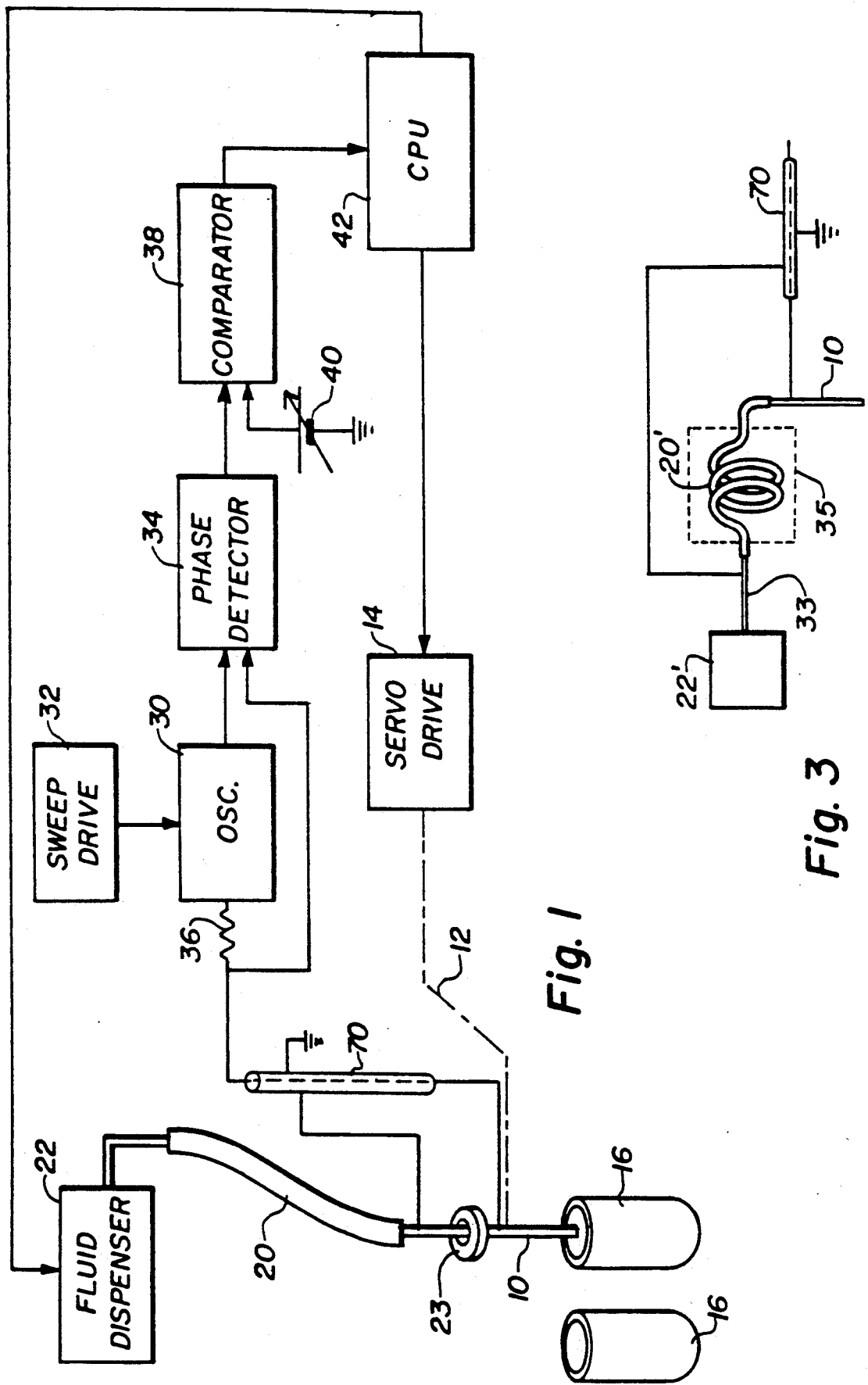
FIG. 1 is a block diagram of a liquid level sensor constructed in accordance with this invention.

Reference is now made to the drawings in which FIG. 1 illustrates a typical probe 10 driven by a robotic arm 12 which is controlled by a servo drive 14 of conventional design. The probe 10, translated in the X, Y, and Z directions by the servo drive 14 of conventional design, is adapted to be moved above and introduced into any one of plural sample or reagent containers 16.

The probe 10 is coupled through a flexible plastic tube 20 to what is designated as a fluid pipettor 22. The fluid pipettor 22 is able to either expel the contents of the probe or suck through the probe the contents of the containers 16. The tubing 20 is made of a suitable chemically inert, flexible plastic such as polypropylene and the probe 10 is made of a suitable chemically inert metal such as platinum or stainless steel. The robotic arm under the control of the servo drive 14 is able to raise and lower the probe 10 so as to dip into and suck fluid from the containers 16 and also move the probe in a translational movement to access in X and Y directions any one of the sample, reagent, or reaction containers 16 (Only two of which are shown.).

In accordance with this invention, a ferrite toroid 23 is positioned around the upper end of the probe 10. The toroid may be an 11-2060B from Ferronics, Inc., Fairport, N.Y. Several may be stacked as required. It may be attached to the probe by hot melt glue or other mechanical fastener. A high frequency oscillator 30 is coupled to the electrically conductive probe 10 through a coaxial cable 70, whose sheath is grounded. The feed from the oscillator is attached to the probe 10 below the toroid 23, i.e., between the probe tip and the toroid. Likewise the grounded sheath of the cable 70 is connected to the upper end of the probe above the toroid. In turn the oscillator, which may be a voltage controlled oscillator (VCO), is connected to a sweep oscillator 32 which preferably provides a linear (e.g., triangular or sawtooth) waveform such that the high frequency oscillator is successively swept through a range of frequencies. Abrupt changes in the probe capacitance are caused when the probe contacts a liquid. Such abrupt changes in capacitance generate a spectrum of frequencies in the output of the detector. The sweep oscillator preferably sweeps the high frequency oscillator frequency at a repetition frequency above those frequency components generated by abrupt changes in probe capacitance. In turn, the oscillator 30, preferably is a voltage controlled oscillator, as noted, or similar oscillator whose frequency can be varied as result of an input signal.

The output of the high frequency oscillator 30 is coupled to a phase detector 34 preferably capable of providing a D.C. output voltage. The high frequency oscillator 30 is coupled through a resistor 36 to the input of the coaxial cable 70 and a connection is made on the probe side of the resistor 36 to the phase detector. In this manner the phase detector is subjected to the shift in phase caused by a change in the dielectric to which the probe is subjected. In other words the dielectric is part of an RC phase shifter. There is a stray capacitance between the probe 10 and liquid in the container 16. The liquid provides a dielectric which is large compared to that of air. When the probe touches the liquid, the higher dielectric constant and greater surface area results in an increased capacitance of the probe to ground. The output of the phase detector is a D.C. signal which varies in amplitude in accordance with the changing capacitance sensed by the probe.

A voltage comparator 38 compares the signal from the phase detector 34 with a reference obtained by an adjustable voltage source 40. The output of the comparator is applied to a central processing unit (CPU) 42 which in turn is programmed to control the servo drive 14 in any conventional manner such as that described in U.S. Pat. No. 4,818,492. It controls the fluid dispenser 22 to suck liquid from the container 16 when the comparator signals that the liquid level has been reached. Thus the central processing unit 42 controls both the position of the probe 10 and whether the probe dispenses or sucks up fluid from a container. Such central processing units are well known and will not be described further since they do not relate directly to the particular invention which is a level sensor.

By thus isolating the probe from the tubing, the effect created by the electrically conductive or high dielectric fluid within the tubing does not affect the sensitivity of the probe during probe movement. The isolation of the tubing with the ferrite toroids greatly facilities the structure of the probe. With the probe grounded, it is easier to connect it to a suitable sturdy mount. Also the tubing is isolated and the amount of the probe that is carrying RF energy is reduced by the grounding of the upper end of the probe. Less RF energy is radiated thereby enabling the instrument to better comply with emission requirements for instruments of this type. The high conductive reactance property of the probe with the toroid serves to essentially decouple electrically the upper end of the probe and its feed line (in the form of tubing 20) from the rest of the probe. Thus the sensitivity of the probe is maintained while at the same time false signals due to the movement of the tubing are virtually eliminated.

Figure 2:
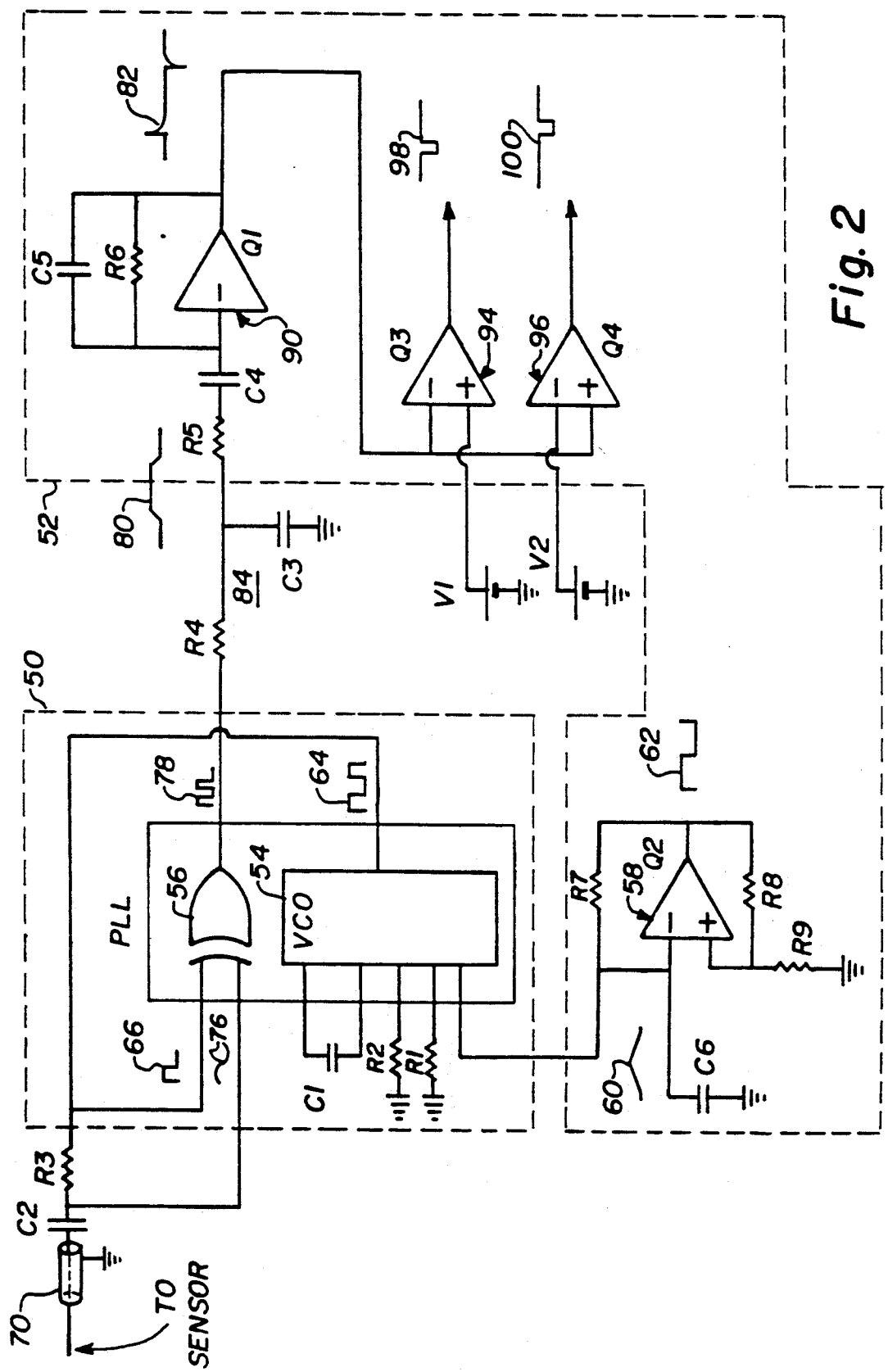
FIG. 2 is a schematic diagram of a preferred embodiment of a liquid level sensor constructed in accordance with this invention.

With reference to FIG. 2, a specific circuit constructed in accordance with the preferred embodiment of this invention for sensing liquid levels is illustrated. In this circuit essentially two integrated circuit chips are used. The first is phase-locked loop (PLL) which may use, for example, a CD4046BM chip made by National Semiconductor. In addition a quad operational amplifier chip made by Texas Instrument Company, TLC274CN may be used. The phase-lock loop integrated circuit is designated by the dashed block 50. Similarly, the quad operational amplifier integrated circuit is designated by the dashed block 52. The phase-locked loop includes a voltage controlled oscillator 54 and several phase comparators only one of which 56 is shown. The voltage controlled oscillator 54 has several external components which have been selected to provide a nominal high frequency of 1 MHz, i.e., by choice of resistors R1 and R2 and capacitor C1. The selection of these values is described in the application notes for the chip from National Semiconductor. Furthermore, the resistors R1 and R2 have been proportioned such that the VCO input will sweep the nominal oscillator frequency 200 kHz at an approximately 20 kHz rate.

The frequency of VCO 54 is caused to change by a sweep oscillator in the form of an astable oscillator which is constructed as part of the quad operational amplifier chip 52. The sweep oscillator, designated 58, is constructed such that the output is applied through resistor R7 and capacitor C6 to the inverting input of the amplifier labelled Q2. Further, the output of Q2 is applied through resistors R8 and R9 to the noninverting input of the amplifier. Its operation is understood by supposing that the output of the amplifier goes high. The voltage at the noninverting input will go high. The voltage at the inverting input will remain low because of capacitor C6. As charge accumulates on capacitor C6 a time will come when its voltage exceeds that of the noninverting input, at which time the output of Q2 will swing low. In a similar fashion resistors R8 and R9 apply a low voltage to the noninverting input of Q2. Because of capacitor C6, the voltage at the inverting input will remain high. This status will remain until the voltage across C6 is discharged to a voltage below that of the noninverting input at which time the output of Q2 will swing high and the cycle will repeat endlessly.

In this circuit it is customary to take the voltage from the output which is a square wave 62. However to obtain a voltage to provide a linear sweep of frequency of the oscillator, a sawtooth or triangular waveform is preferred. This is the signal found at the junction of R7 and C6. This approximately triangle wave 60 is applied to the VCO 54 input. This signal causes the voltage controlled oscillator to sweep approximately 200 kHz around the nominal 1 MHz frequency. The rate at which it sweeps up and down is approximately 20 kHz and is determined by the values of the resistors $R_7$, $R_8$, $R_9$, and C6.

The output of the voltage controlled oscillator 54 is designated by the square waveform 64. The output of the VCO is applied to two portions. One portion is supplied to a phase comparator 56. This serves as the reference signal and is illustrated by the waveform 66. The other portion of the output of the VCO is supplied to an RC phase shifter composed of elements R3, C2 and the probe. Capacitor C2 is used as the D.C. blocking capacitor. The actual capacitance affecting the phase shift is comprised of the capacitance of the coaxial cable labelled 70 and the capacitances to ground of the probe. The probe is metal as described. It may have plastic tubing 74 which is attached to a pump (not shown). At the junction between R3 and C2 is a signal labelled 76 that is affected by the dielectric of the sample whose level is sought. The signal 76 affection depicts a change in amplitude and/or phase over that of waveform 64, the degree of change being a function of the sample dielectric. This signal 76 is an approximate triangle wave and is applied to the signal input of phase comparator 56.

Phase comparator 56 is of the "exclusive OR" variety. The output of the phase comparator is a series of pulses, the width of which depends on the phase difference between the reference signal 66 and the input signal 76. The output of the phase comparator 56, in the form of a pulse train 78, is applied to an RC filter network 84 composed of resistor R4 and capacitor C3. The purpose of this filter is to remove the pulses from the phase comparator output and produce an approximate D.C. level proportionate to the area of the waveform 78. If the pulse width of 78 changes then the approximate D.C. level of the filter 84 will change. The changing D.C. level is represented by the waveform 80 which is applied to a differentiator 90, the heart of which is an operational amplifier Q1, a member of the quad operational amplifier 52. Thus, to effect the differentiation, the output of the RC filter 84 is applied through resistor R5 and capacitor C4 to the input of the amplifier 90. The feedback portion of the amplifier 90 is composed of R6 and C5 in parallel. These components have been selected to form a differentiator for low frequencies, namely the changing portion of waveform 80. These components also filter out high frequency noise that might leak through the filter network 84.

The output of the differentiator 90 is in the form of pulses, the height of which is dependent on the rate of change and extent of change of waveform 80. This output signal is represented by the waveform 82. These pulses can then be discriminated with a window comparator to select pulses of sufficient amplitude to represent a meaningful transition in the capacitances at the probe which, of course, is sensitive to the dielectric effect of the sample level. The window comparator is composed of amplifiers of operational amplifiers 52 labelled 94 and 96. In these amplifiers the signal level is compared against the voltage labelled V1 and V2. For example, if the input voltage to 94 is applied to the inverting input, whenever the input voltage is below V1 the output will be high. For the period of time that the input voltage rises above V1, the output will remain low. Thus, the positive going pulse in waveform 82 causes a negative going pulse in waveform 98. In a similar fashion the negative going pulse in waveform 82 appears as a negative going pulse from circuit 96 and has a waveform labelled 100. The two waveforms 98 and 100 are the outputs of the circuit. Waveform 98 has a negative going pulse whenever the probe encounters an increase in capacitance as when it touches a liquid. Waveform 98 has a negative going pulse whenever the probe encounters a liquid of increased conductance or dielectric constant. In a similar fashion waveform 100 is a negative going pulse whenever the probe decreases in capacitance, for example, when the probe is withdrawn from a fluid of high dielectric or conductance properties.

While the preferred embodiment of the invention described uses a phase detector and RC phase shift circuit it is to be understood that any of the devices known in the prior art using a source of oscillations for detecting small changes in capacitance at the probe may be used.

In an alternative embodiment of this invention, as depicted in FIG. 3, instead of a toroid the tubing 20' may be coiled. The tubing contains an electrically conductive fluid which forms the coil and whatever RF energy appears at the probe 10 tends to be blocked from passing through the high inductance provided by the coiled tubing 20'. In this embodiment it is desirable to connect the plastic tubing 20' through a small piece of metal tubing 33 to provide a ground for the conductive liquid in the tubing. The grounded metal tubing 33 should be between the fluid dispenser 22' and the coiled tubing 20'.

In an alternative embodiment, to improve the inductance of the coil 20', the coil may be installed in a ferrite pot core 35 depicted by the dashed lines. The ferrite pot core is a material 3622P-LOO-3B7 from Ferroxcube Saugerties, N.Y. The tubing was wound in two layers of four turns each for insertion into the pot core. Metal tubing may be used instead of plastic for that purpose. In which event the metal tubing must be insulated to avoid short circuiting the turns of the conductor.

What is claimed is:

1. In a capacitive liquid level sensor for determining the liquid level of a sample in a liquid pipetting system, having:

a pipette probe for withdrawing liquid from a sample,
    means including tubing coupled to the pipette probe for applying suction,
    an oscillator coupled to the probe for applying a high frequency signal to the probe to create a second signal whose amplitude and/or phase is determined by the capacitance of the probe; and
    comparator means for generating a level sensor signal according to the amplitude or phase of the second signal for signaling the probe's reaching the liquid level of the sample, the improvement comprising:
    means exhibiting an inductive reactance positioned on the pipette probe adjacent to the suction means, thereby to electrically isolate the probe from the suction means, the tubing for applying suction being plastic tubing and a portion being coiled in a ferrite core to provide the means exhibiting inductive reactance.

2. The liquid level sensor of claim 1 wherein an electrically conductive piece of tubing is connected adjacent to the plastic tubing opposite to the probe.

* * * * *